United States Patent
Blue

(10) Patent No.: US 10,180,777 B2
(45) Date of Patent: *Jan. 15, 2019

(54) HEALTHCARE SIMILARITY ENGINE DASHBOARD

(71) Applicant: Optum, Inc., Minnetonka, MN (US)

(72) Inventor: Joseph Blue, Minnetonka, MN (US)

(73) Assignee: Optum, Inc., Minnetonka, MN (US)

( * ) Notice: Subject to any disclaimer, the term of this patent is extended or adjusted under 35 U.S.C. 154(b) by 952 days.

This patent is subject to a terminal disclaimer.

(21) Appl. No.: 14/476,420

(22) Filed: Sep. 3, 2014

(65) Prior Publication Data

US 2016/0063214 A1 Mar. 3, 2016

Related U.S. Application Data

(63) Continuation of application No. 14/476,287, filed on Sep. 3, 2014.

(51) Int. Cl.
*G06F 19/00* (2018.01)
*G06F 3/0484* (2013.01)
(Continued)

(52) U.S. Cl.
CPC ...... *G06F 3/04842* (2013.01); *G06F 3/04845* (2013.01); *G06F 3/04847* (2013.01);
(Continued)

(58) Field of Classification Search
CPC ........ G06Q 50/22; G06Q 50/24; G16H 50/20; G16H 50/70; G16H 50/50; G16H 10/60;
(Continued)

(56) References Cited

U.S. PATENT DOCUMENTS

2006/0129427 A1 6/2006 Wennberg
2009/0131758 A1* 5/2009 Heywood ............ A61B 5/0002
600/300
(Continued)

FOREIGN PATENT DOCUMENTS

WO WO 2014/052921 A2 4/2014

OTHER PUBLICATIONS

Office Action for U.S. Appl. No. 14/476,287 dated Sep. 28, 2017, 15 pages.
(Continued)

*Primary Examiner* — Maroun P Kanaan
(74) *Attorney, Agent, or Firm* — Alston & Bird LLP

(57) ABSTRACT

In general, embodiments of the present invention provide systems, methods and computer readable media for a healthcare similarity engine that uses healthcare data to identify a set of similar patients. One aspect of the subject matter described in this specification can be embodied in methods that include the actions of receiving a similarity request including a patient X data vector representing attributes of a particular patient X and a set of similarity parameters; calculating a set of similarity metrics using the patient X data vector and the set of similarity parameters; ranking the population of patients based on their respective similarity metrics; and generating a neighborhood subset of the population of patients most similar to patient X by selecting the top-ranked patients. Another aspect of the subject matter can be embodied in methods that include the actions of providing a display of a graphical representation of a healthcare similarity request input dashboard.

20 Claims, 12 Drawing Sheets

(51) Int. Cl.
  *G06F 17/30* (2006.01)
  *G16H 50/70* (2018.01)
  *G16H 10/60* (2018.01)
  *G16H 50/20* (2018.01)

(52) U.S. Cl.
  CPC .... *G06F 17/3053* (2013.01); *G06F 17/30324* (2013.01); *G06F 19/00* (2013.01); *G16H 50/70* (2018.01); *G16H 10/60* (2018.01); *G16H 50/20* (2018.01)

(58) Field of Classification Search
  CPC ................ G06F 19/321; G06F 19/325; G06F 17/30592; G06F 17/30958; G06F 19/324; G06F 17/30324; G06F 3/04847; G06F 17/30277; A61B 5/742
  See application file for complete search history.

(56) References Cited

U.S. PATENT DOCUMENTS

2010/0131293 A1* 5/2010 Linthicum ............ G06Q 50/22 705/3
2012/0041772 A1  2/2012 Ebadollahi et al.
2013/0272593 A1  10/2013 Lee et al.

OTHER PUBLICATIONS

Office Action for U.S. Appl. No. 14/476,287 dated Dec. 15, 2016, 15 pages.
Final Rejection dated Mar. 19, 2018 for U.S. Appl. No. 14/476,287.
International Search Report and Written Opinion for corresponding International Application No. PCT/IB2015/056543, dated Dec. 17, 2015.

* cited by examiner

Focused Care Example

My Patient's History

| Code | Age | Condition |
|---|---|---|
| 493300 | 42 | Chronic obstructive pulmonary disease |
| 473300 | 42 | Inflammation of esophagus |
| 493800 | 42 | Asthma |
| 712211 | 43 | Joint degeneration localized — neck |
| 353100 | 44 | Hypertension |
| 779300 | 44 | Prophylactic proc other than inoculation |
| 714611 | 44 | Minor orthopedic trauma — neck |
| 164400 | 45 | Gout |
| 473400 | 46 | Irritable bowel syndrome |
| 353700 | 47 | Other & unspec disorders of eye & adnexa |
| 712200 | 48 | Osteoporosis |
| 712208 | 48 | Joint degeneration localized — back |
| 714911 | 48 | Other minor orthopedic disorders — neck |
| 403500 | 48 | Chronic sinusitis |
| 437400 | 48 | Bacterial lung infections |
| 164700 | 49 | Hyperlipidemia other |
| 523200 | 49 | Other diseases of hepatobiliary system |

Common Problems among patients like mine

| Prob | Pop | Condition |
|---|---|---|
| 55% | 28% | Other minor ortho disorders — back |
| 43% | 32% | Hyperlipidemia other |
| 39% | 26% | Acute sinusitis |
| 28% | 24% | Tonsillitis adenoiditis or pharyngitis |
| 27% | 17% | Allergic rhinitis |
| 24% | 23% | Other inflammation of skin |

Potential Concerns for patients like mine

| Rel | Abs tot | Yrs | Condition |
|---|---|---|---|
| +93% | +26% | 3 | Other minor ortho disorder — back |
| +267% | +13% | 7 | Gastritis &/or duodenitis |
| +48% | +12% | 7 | Acute sinusitis |
| +119% | +11% | 8 | Minor ortho trauma — back |
| +224% | +10% | 9 | Major joint inflam — other |
| +57% | +10% | 9 | Allergic rhinitis |
| +111% | +9% | 10 | Viral meningitis |

FIG. 8

Treatment Pathway Example

*Member Claims & Prescriptions Filled by Year*

| Year | Physician | Facility | Prescriptions Filled (Generic) |
|---|---|---|---|
| 2006 | Mood disorder nec, Parasitic skin inf, Ear infect dis, contact dermatitis, non-rh neoplasm | AIDS, bacterial infect skin, skin trauma (not burn) | lexapro, wellbutrin, ambien, lindane, permethrin, doxycycline hyclate, clobetasol propionate |
| 2007 | Hernia ext hiatal, acute sinusitis, closed fracture – wrist, other infect dis. | <N/A> | ambien, valtrex, tussionex, levaquin |
| 2008 | Acute sinusitis, exp to infect dis. | <N/A> | ambien, valtrex, levaquin |
| 2009 | Exp to infect dis. | Viral pneumonia | ambien, valtrex, azithromycin, benzonatate |
| 2010 | Exp to infect dis. | <N/A> | ambien, bupropion, valacyclovir |
| 2011 | Male sex gland dis., acute sinusitis, exp to infect dis, minor infect pulmonary dis. | AIDS, Male sex gland dis, cardiovascular dis S & S | ambien, valacyclovir, celebrex, finasteride, levaquin, indomethacin, fluticasone propionate |

*Common Prescriptions Among Similar Members by Condition:*

| Condition | Prescriptions Filled Among Similar Members (ranked by patients treated) |
|---|---|
| AIDS | Therapeutic Area 1 (popular generics), Therapeutic Area 2 (popular generics), etc. |
| Male sex gland disorder | Therapeutic Area 3 (popular generics), Therapeutic Area 1 (popular generics), etc. |
| Viral pneumonia | Therapeutic Area 10 (popular generics), Therapeutic Area 4 (popular generics), etc. |
| Acute sinusitis | Therapeutic Area 3 (popular generics), Therapeutic Area 2 (popular generics), etc. |

FIG. 9

HEALTHCARE SIMILARITY ENGINE DASHBOARD

CROSS-REFERENCE TO RELATED APPLICATIONS

This application is a continuation of the following application: U.S. application Ser. No. 14/476,287, filed Sep. 3, 2014, entitled "HEALTHCARE SIMILARITY ENGINE," listing Joseph Blue as inventor.

FIELD

Embodiments of the invention relate, generally, to a healthcare similarity engine that uses healthcare data to identify a set of similar patients.

BACKGROUND

Solutions in healthcare (e.g., focused patient care, treatment, risk adjustment, and health improvement scenarios) often are based on inferences derived from studies of data describing healthcare attributes of patient populations. Typically, the inferences are limited by the data available for the studies (e.g., the number of covered lives and/or the number of data sources). Additionally, performing a study is both time and resource intensive.

Current methods for generating a study exhibit a plurality of problems that make current systems insufficient, ineffective and/or the like. Through applied effort, ingenuity, and innovation, solutions to improve such methods have been realized and are described in connection with embodiments of the present invention.

SUMMARY

In general, embodiments of the present invention provide herein systems, methods and computer readable media for generating a study that uses input data representing attributes of a particular patient and a set of similarity factors to identify a set of similar patients represented within a data repository describing attributes of a large patient population.

In general, one aspect of the subject matter described in this specification can be embodied in computer-implemented methods that include the actions of responsive to receiving a similarity request including a patient X data vector representing attributes of a particular patient X, a set of one or more similarity parameters, and at least one neighborhood size parameter, calculating a set of similarity metrics using the patient X data vector and the set of similarity parameters; ranking the population of patients based on their respective similarity metrics; and generating a neighborhood subset of the population of patients most similar to patient X by selecting the top-ranked patients from the population.

These and other embodiments can optionally include one or more of the following features. Calculating the similarity metric representing the similarity between patient X and the patient within the population of patients may include the actions of receiving a data vector representing attributes of the patient within the population of patients; generating a set of parameter-specific similarity factors by performing operations that may include actions calculating, for each of the set of similarity parameters, an associated parameter-specific similarity factor by applying a parameter-specific function to the patient X data vector and the data vector representing attributes of the patient within the population of patients; and calculating the similarity metric as a linear sum of the set of parameter-specific similarity factors. The parameter-specific function may be selected from a group of Boolean preferences including log likelihood function and Tanimoto similarity. The parameter-specific function may be a Pearson correlation function. Calculating the similarity metric may further include normalizing the similarity metric to the range of 0,1. In embodiments in which each of the set of similarity parameters is respectively associated with a weight, calculating the parameter-specific similarity factor for each similarity parameter may further include multiplying the parameter-specific similarity factor by the weight associated with the similarity parameter. Calculating the similarity metric representing the similarity between patient X and the patient within the population of patients may further include deriving at least one inference based at least in part on attributes of the subset of the population of patients most similar to patient X; and using the derived inference by at least one healthcare application selected from a group of healthcare applications including focused care, treatment pathways, treatment optimization clinical pathways, risk adjustment, abuse, and health improvement scenarios. The set of similarity parameters may be selected from a group of similarity parameters including patient co-morbidity, disease chronology, disease rareness, disease pharmaceutical history, and patient clinical data. The neighborhood size parameter may be selected from a group of neighborhood size parameters including a maximum size of the neighborhood to be generated and/or a minimum similarity metric value to be associated with the neighborhood.

In general, another aspect of the subject matter described in this specification can be embodied in computer-implemented methods that include the actions of providing a display of a graphical representation of a healthcare similarity request input dashboard, wherein the graphical representation includes a set of interactive regions comprising widgets, and wherein the interactive regions include a similarity parameter input region, a neighborhood size parameter input region, and a similarity request input region; and in response to a user-interaction with at least one submission widget displayed in the similarity request input region, generating a similarity request including a patient X data vector representing attributes of a particular patient X, a set of one or more similarity parameters, and at least one neighborhood size parameter.

These and other embodiments can optionally include one or more of the following features. In embodiments in which the similarity parameter input region includes similarity widgets representing one or more similarity parameters, and generating the similarity request may include the actions of receiving user input from the similarity widgets; and generating the set of similarity parameters based on the user input. In embodiments in which the similarity widgets include a patient co-morbidity region including a set of checkbox widgets each associated with a particular disease, generating the set of similarity parameters may include the actions of identifying a set of diseases respectively associated with a user-selected checkbox; generating a co-morbidity similarity parameter using the identified set of diseases; and adding the co-morbidity similarity parameter to the set of similarity parameters. In embodiments in which the similarity widgets include at least one meter widget associated with a particular similarity parameter, generating the set of similarity parameters may include the actions of adding the particular similarity parameter to the set of similarity parameters based on a user-selected importance indicator represented by the meter. Adding the particular similarity parameter to the set of similarity parameters may include associating a weight with the particular similarity parameter based on a user-selected importance indicator represented by the meter. In embodiments in which the neighborhood size parameter input region includes at least one neighborhood size widget representing at least one neighborhood size parameter, generating the similarity request may include the actions of receiving user input from the neighborhood size widget; and generating the neighborhood size parameter based on the user input. In embodiments in which the neighborhood size widget is a meter widget and the neighborhood size parameter is maximum neighborhood size, generating the similarity request may include the actions of receiving a user-selected maximum neighborhood size from the neighborhood size widget; and generating the maximum neighborhood size parameter using the user-selected maximum neighborhood size. In embodiments in which the neighborhood size widget is a meter widget, and the neighborhood size parameter is minimum similarity metric threshold, generating the similarity request may include the actions of receiving a user-selected minimum similarity metric threshold from the neighborhood size widget; and generating the minimum similarity metric threshold parameter using the user-selected minimum similarity metric threshold.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

FIG. 8 illustrates a "Focused Care for My Patient" application in which the efficiency of the encounter between a provider/practitioner and a patient is improved in accordance with some embodiments discussed herein;

FIG. 9 illustrates an example of Treatment Pathways application in which a provider is informed as to how similar patient's treatments progressed and/or gaps in care may be highlighted in accordance with some embodiments discussed herein;

DETAILED DESCRIPTION

Figure 1:
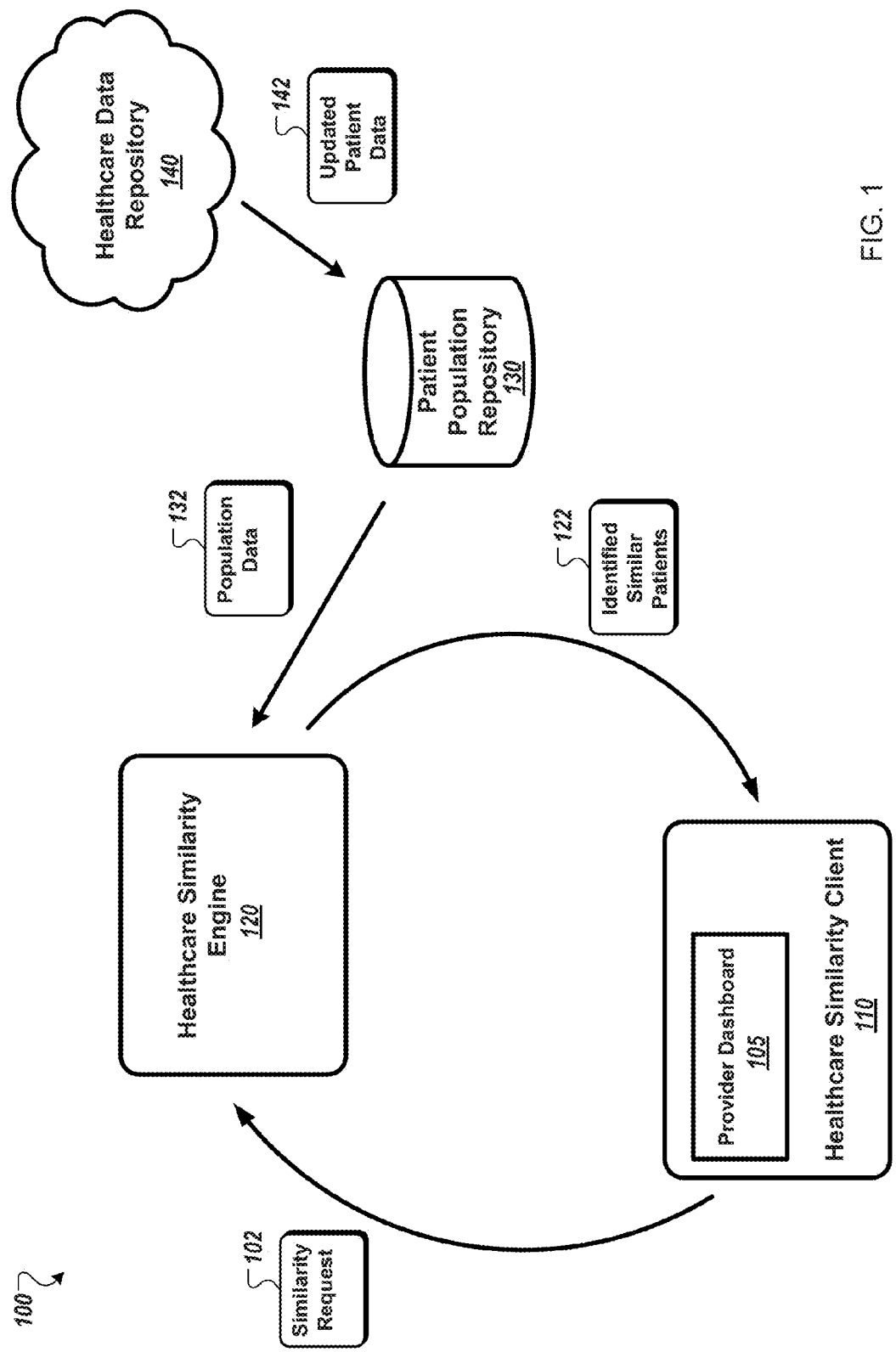
FIG. 1 illustrates an example system that can be configured to implement dynamically generating a set of patients that have healthcare attributes that are similar to a particular patient in accordance with some embodiments discussed herein.

Embodiments of the present invention now will be described more fully hereinafter with reference to the accompanying drawings, in which some, but not all embodiments of the invention are shown. Indeed, this invention may be embodied in many different forms and should not be construed as being limited to the embodiments set forth herein; rather, these embodiments are provided so that this disclosure will satisfy applicable legal requirements. The term "or" is used herein in both the alternative and conjunctive sense, unless otherwise indicated. The terms "illustrative," "exemplary," and "example" are used to be examples with no indication of quality level. Like numbers refer to like elements throughout Like numbers refer to like elements throughout.

As described herein, system components can be communicatively coupled to one or more of each other. Though the components are described as being separate or distinct, two or more of the components may be combined into a single process or routine. The component functional descriptions provided herein including separation of responsibility for distinct functions is by way of example. Other groupings or other divisions of functional responsibilities can be made as necessary or in accordance with design preferences.

As used herein, the terms "data," "content," "information" and similar terms may be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data may be received directly from the another computing device or may be received indirectly via one or more intermediary computing devices, such as, for example, one or more servers, relays, routers, network access points, base stations, and/or the like. Similarly, where a computing device is described herein to send data to another computing device, the data may be sent directly to the another computing device or may be sent indirectly via one or more intermediary computing devices, such as, for example, one or more servers, relays, routers, network access points, base stations, and/or the like.

Solutions in healthcare are based on inferences that often are limited by the data available (e.g., the number of covered lives and/or the number of data sources). Additionally, the inferences are often population-based rather than being individual-based because predictive models typically used to generate the inferences (e.g., regression, decision trees) are population-based.

Recommender engines are powerful "big-data" engines that provide suggestions, quickly gleaned from massive amounts of data, to individual users. Recommendation engines are often used to provide solutions in numerous customer and item-based settings (e.g., books, movies, songs, web pages. In embodiments, a healthcare similarity engine is an adaptation of a traditional recommender engine algorithm that is used to provide inferences about individual members in a healthcare setting.

As such, and according to some example embodiments, the systems and methods described herein are therefore configured to provide inferences dynamically about individual members in a healthcare setting in response to receiving input data from a requestor that include a set of health-related factors that the requestor deems important plus at least one parameter that conveys inclusivity of a number of comparable members (a "neighborhood") from which the inferences are derived. In some embodiments, a requestor may input data by interacting with a provider dashboard graphical user interface (GUI).

FIG. 1 illustrates an example system 100 that can be configured to implement dynamically generating a set of patients that have healthcare attributes that are similar to a particular patient. In embodiments, system 100 comprises a healthcare similarity client 110, configured to generate a similarity request 102 in response to receiving input data that may include healthcare attributes of a particular patient as well as configuration data that may include a set of one or more similarity parameters; and a healthcare similarity engine 120, configured to respond to receipt of a similarity request by using the data included in the similarity request to select a set of patients 122 determined to be similar to the particular patient based on their respective healthcare attributes. In some embodiments, the identified similar patients 122 are selected using a set of patient population healthcare data 132 that is collected from a patient population repository 130 that stores updated patient data 142 received from a healthcare data repository 140. In some embodiments, healthcare similarity client 110 includes a provider dashboard 105, configured to receive the input data used to generate the similarity request 102.

Figure 2:
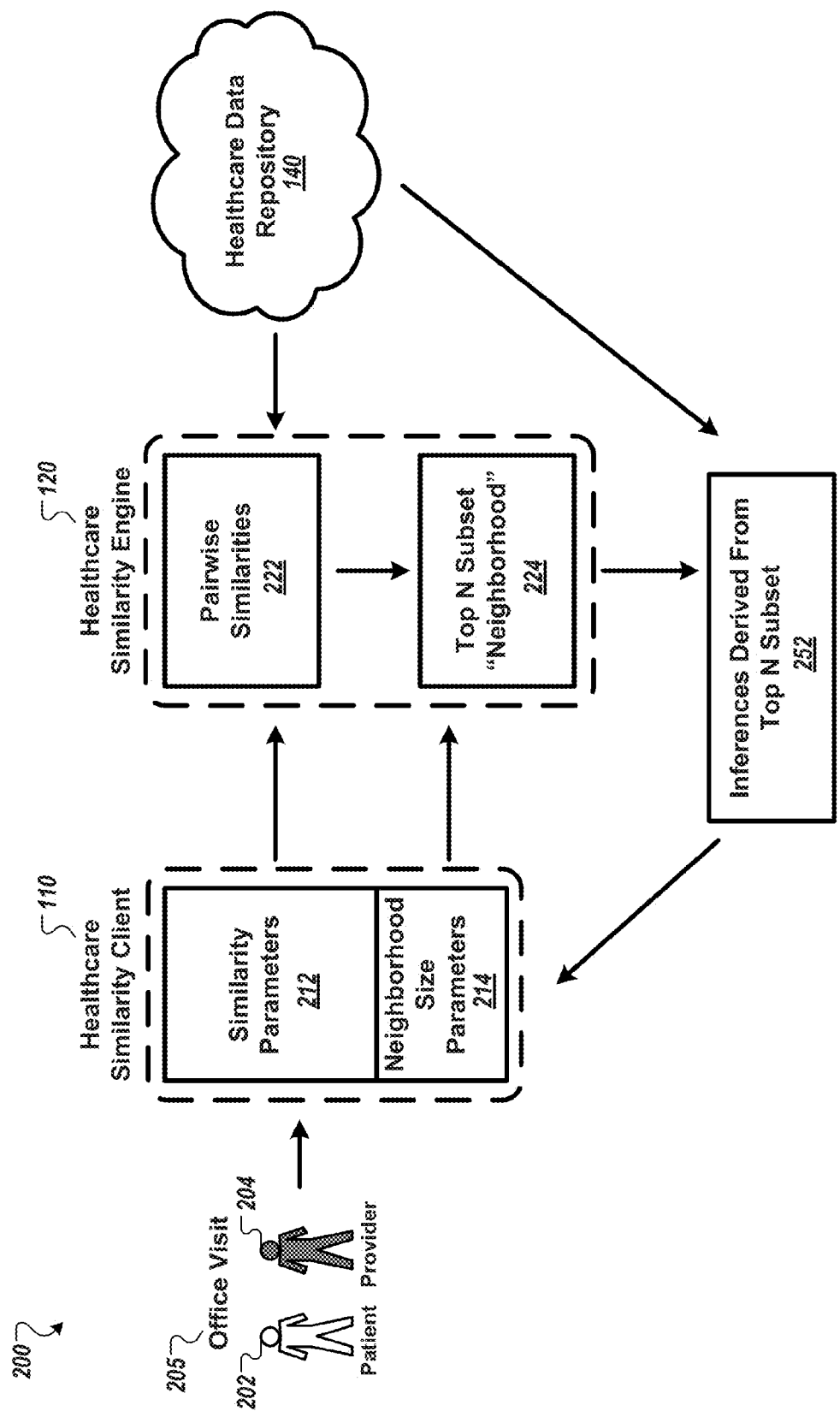
FIG. 2 illustrates an exemplary workflow for generating a set of patients that have healthcare attributes that are similar to a particular patient in accordance with some embodiments discussed herein.

FIG. 2 illustrates an exemplary workflow 200 for generating a set of patients that have healthcare attributes that are similar to a particular patient. Workflow 200 is presented for illustration and not limitation, and represents a scenario in which generating the set of similar patients is initiated on behalf of a particular patient 202 by a provider 204 (e.g., a physician or other healthcare practitioner) during an office visit 205. In some embodiments, workflow 200 may be implemented using system 100.

In embodiments, the healthcare similarity client 110 receives input data from the provider 204. In some embodiments, the provider 204 may interact with a provider dashboard interface 105 to specify the input data. In some embodiments, the provider dashboard interface 105 may be presented as a graphical user interface (GUI, hereinafter) containing interactive widgets for collecting input data. An exemplary provider dashboard interface 105 implemented as a GUI will be described in detail with reference to FIG. 7.

In embodiments, the input data may include healthcare attributes of the patient (e.g., the patient's age, gender, and a set of co-morbidities collected from the patient's 202 history). In some embodiments, the input data may further include configuration data that include a set of one or more similarity parameters 212 upon which the determination of patients similar to the particular patient 202 is based and, additionally and/or alternatively, one or more neighborhood size parameters 214.

In embodiments, exemplary similarity parameters 212 may include disease chronology, disease rareness, disease pharmaceutical history, patient behaviors, patient demographics and patient clinical data (e.g., vital signs). In some embodiments, feature extraction of the input patient healthcare attributes may be performed and, as a result, an input patient feature vector may be generated that represents attributes of the patient 202. In some embodiments, the feature extraction is based at least in part on the input similarity parameters 212. In some embodiments, the input patient feature vector is generated by the healthcare similarity client 110 in response to receiving the input data, and the input patient feature vector is transmitted to the healthcare similarity engine 120 for processing. In some alternative embodiments, the input patient feature vector is generated by the healthcare similarity engine 120 in response to receiving the input data from the healthcare similarity client 110. The implementation choice for calculating/determining the input patient feature vector is not critical to embodiments the invention.

In embodiments, pairwise similarities 222 are calculated/determined between the patient 202 and each of a population of patients for whom healthcare attributes have been collected previously and stored within a healthcare data repository 140. In some embodiments, calculation/determination of similarity between the patient 202 and a patient within the population of patients includes generating a feature vector for the population patient and performing a similarity calculation/determination using the input patient feature vector and the generated feature vector for the population patient. In some embodiments, calculation/determination of similarity between the patient 202 and a population patient results in a similarity metric that represents the amount of similarity between the pair of patients. An exemplary method for calculation/determination of a similarity metric will be described in detail with reference to method 500.

In some embodiments, the patients in the population of patients are associated with their respective similarity metrics, and the population of patients may be ranked based at least in part on their associated similarity metrics. In some embodiments, a subset of the top-ranked patients 224 (a "neighborhood" hereinafter) may be selected from the population of patients.

In some embodiments, the size N of the neighborhood may be determined based at least in part on one or more input neighborhood size parameters 214. In embodiments, exemplary neighborhood size parameters 214 may include a maximum size of the neighborhood to be returned in the generated study and/or a minimum similarity metric value to be associated with the selected subset of the top-ranked patients.

In embodiments, a study including one or more inferences 252 may be derived from attributes of the generated neighborhood, and the study may provide the basis for a variety of different types of healthcare applications in use by the requestor who submits the similarity request 102 to the system 100. A set of application examples, provided for illustration and not for limitation, will be described with reference to FIGS. 8-11.

In some embodiments, an application may generate a presentation of the study results to be returned to the requestor who submitted the similarity request 102. In some embodiments, the healthcare similarity client 110 may be executed as an application component while, in some alternative embodiments, the healthcare similarity client 110 may be executed as a component of system 100 that is invoked remotely by one or more applications. Application configuration is implementation dependent, and not critical to embodiments of the invention.

Figure 3:
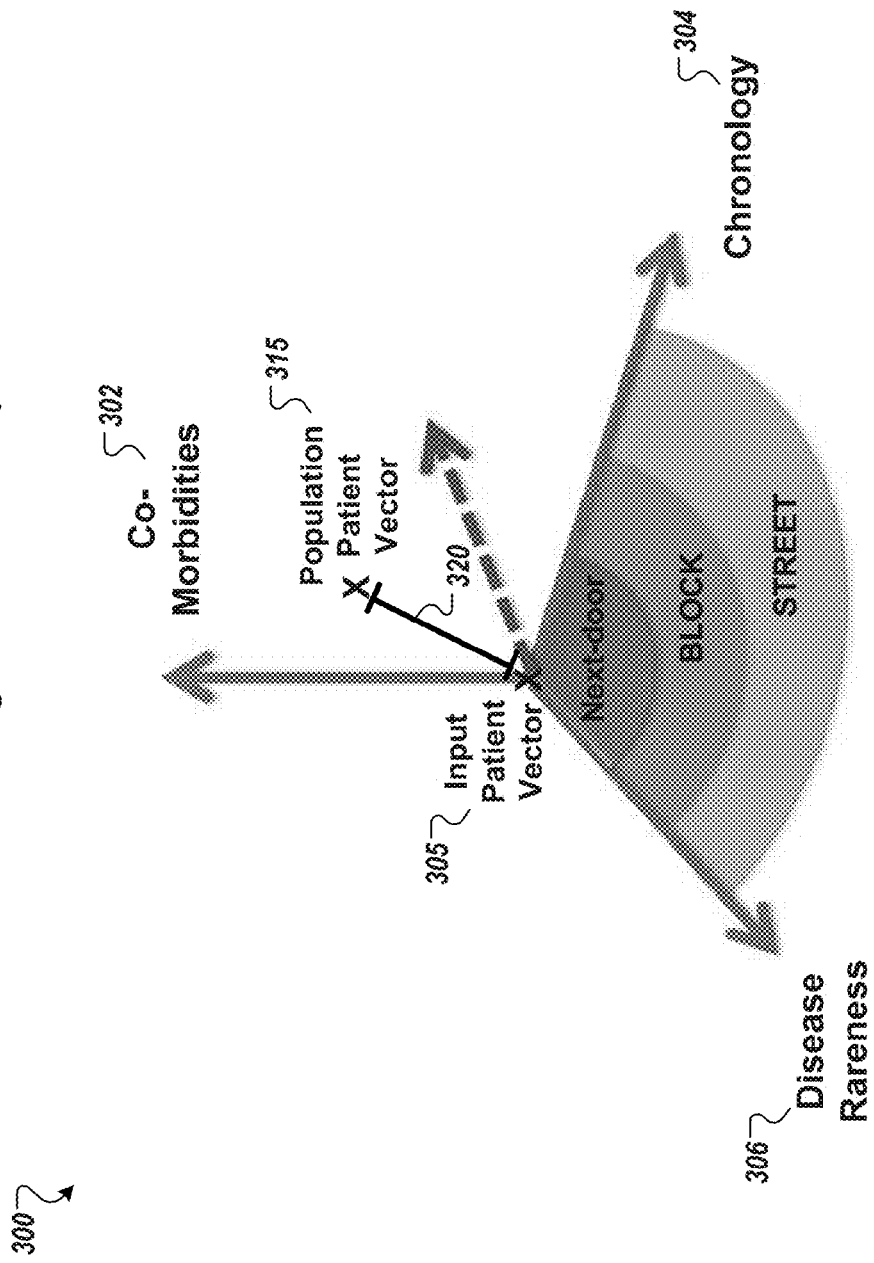
FIG. 3 is an illustration of an example neighborhood generated by a healthcare similarity engine for a particular patient in accordance with some embodiments discussed herein.

FIG. 3 is an illustration of an example neighborhood 300 generated by a healthcare similarity engine for a particular patient. Typically, a healthcare repository (e.g., repository 140) stores data describing a wide variety of types of healthcare data collected for very large patient populations, and it is both computationally difficult and resource-intensive to perform analyses that identify particular trends in particular subsets of the repository data. In embodiments, a neighborhood represents a view of a patient population data repository (e.g., repository 130) that is constructed dynamically in response to a similarity request that includes parameters (e.g., similarity parameters 212 and neighborhood size parameters 214) that are important to the requestor who initiated the similarity request.

Example 300 illustrates a neighborhood within a 3 dimensional feature space defined by similarity parameters representing co-morbidities 302, chronology 304, and disease rareness 306. In embodiments, an input patient feature vector 305 describing healthcare attributes of a particular patient (e.g., patient 202) is instantiated as the center of the multi-dimensional feature space.

In embodiments, feature vectors respectively representing each patient in a population of patients may be mapped into the multi-dimensional feature space, and the similarity metric calculated/determined from a pairwise comparison of the input patient feature vector 305 and a population patient feature vector 315 represents the distance 320 between the pair of vectors within the feature space. Vectors separated by a smaller distance may be considered to be closer neighbors than vectors separated by a larger distance. In embodiments, the input neighborhood size parameters may be used to set the neighborhood boundary (i.e., define a maximum distance between a population patient vector and the input patient vector that is center of the multi-dimensional feature space).

In some embodiments, the neighborhood boundaries may be set to default values. In some alternative embodiments, the neighborhood boundaries (i.e., next door, on the same block, or on the same street) may be set as input parameters based on the type of inferences a requestor intends to make based on attributes the neighborhood. For example, if an inference is to be based on statistical significance, the neighborhood boundaries can be set to include as large a sample size of similar patients as possible. In some embodiments, a requestor may re-submit a similarity request with updated neighborhood size parameters (e.g., increasing the maximum distance and/or the minimum similarity metric) if the initially generated neighborhood is insufficient to support the requestor's intended inferences.

Figure 4:
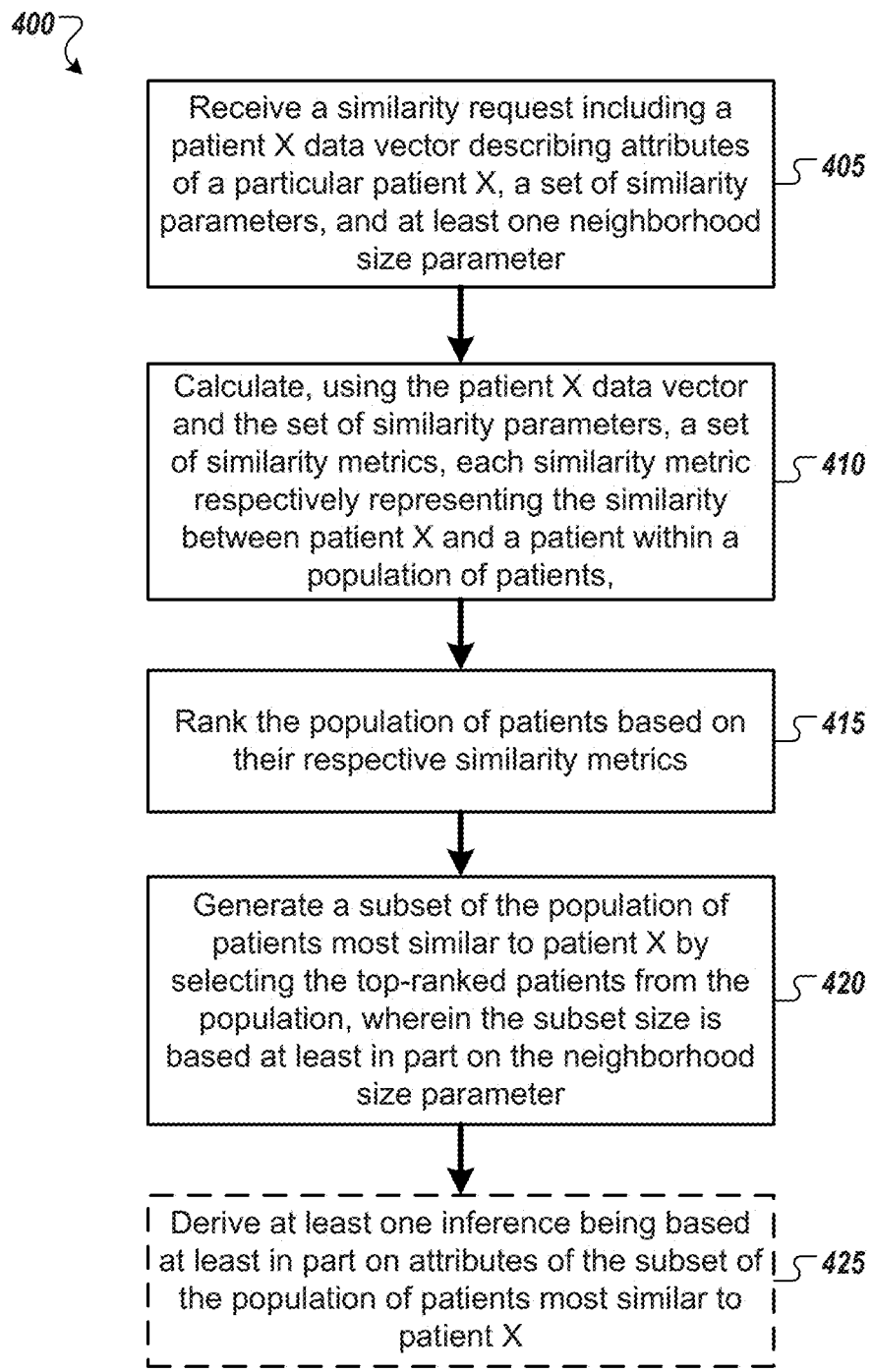
FIG. 4 is a flow diagram of an example method for generating a neighborhood associated with a particular patient in response to receiving a similarity request in accordance with some embodiments discussed herein.

FIG. 4 is a flow diagram of an example method 400 for generating a neighborhood associated with a particular patient in response to receiving a similarity request. For convenience, the method 400 will be described with respect to a system that includes one or more computing devices and performs the method 400. Specifically, the method 400 will be described with respect to processing of a similarity request 102 by healthcare similarity engine 120.

In embodiments, the system receives 405 a similarity request including a patient X feature vector representing attributes of a particular patient X, a set of one or more similarity parameters, and at least one neighborhood size parameter. As previously described, exemplary similarity parameters may include 212 may include disease chronology, disease rareness, disease pharmaceutical history, patient behaviors, patient demographics and patient clinical data (e.g., vital signs), and exemplary neighborhood size parameters may include a maximum size of the neighborhood to be generated and/or a minimum similarity metric value to be associated with the neighborhood.

In embodiments, the system, using healthcare data previously collected from a population of patients and retrieved from a healthcare data repository, calculates 410 a set of similarity metrics, where each similarity metric is respectively associated with a patient from the population of patients and represents the similarity between the patient X and the population patient. In some embodiments, calculating/determining a similarity metric includes calculating/determining a population patient feature vector representing attributes of the population patient in terms of the features represented in the patient X feature vector, and then calculating/determining the similarity metric using the pair of feature vectors. An exemplary method for calculating/determining a similarity metric using a pair of patient healthcare attribute feature vectors is described in detail with reference to FIG. 5.

In embodiments, the system ranks 415 the population of patients based on their respectively associated similarity metrics, and generates 420 a neighborhood by selecting a subset of the top-ranked population of patients. In some embodiments, the neighborhood size is determined based at least in part on at least one neighborhood size parameter. For example, in embodiments, a first neighborhood size parameter may be a maximum total of the population patients to include in the neighborhood, while, additionally and/or alternatively, a second neighborhood size parameter may be a minimum similarity metric value associated with a patient to be included in the neighborhood.

In embodiments, the system optionally derives 425 at least one inference being based at least in part on attributes of the generated neighborhood. As previously described with reference to workflow 200, in some embodiments, a study including one or more inferences may provide the basis for a variety of different types of healthcare applications in use by the requestor who submits the similarity request to the system.

Figure 5:
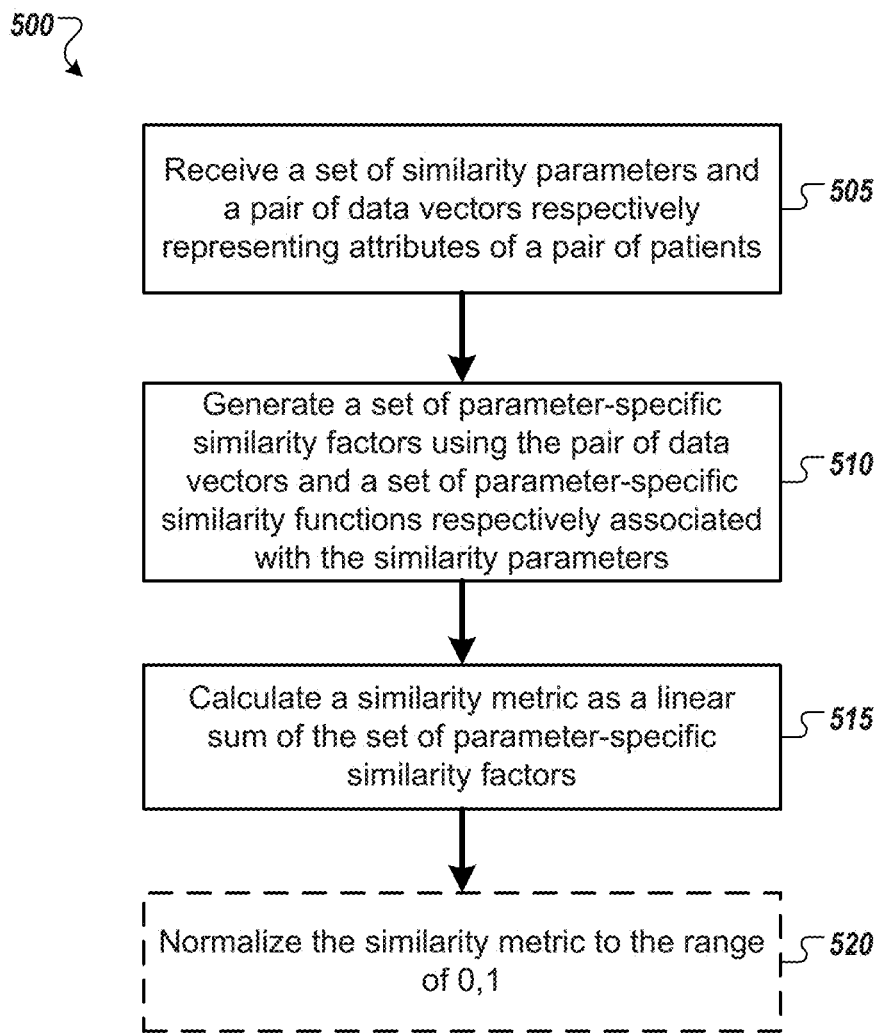
FIG. 5 is a flow diagram of an example method for calculating/determining a similarity metric using a pair of patient healthcare attribute feature vectors in accordance with some embodiments discussed herein.

FIG. 5 is a flow diagram of an example method 500 for calculating/determining a similarity metric using a pair of patient healthcare attribute feature vectors. For convenience, the method 500 will be described with respect to a system that includes one or more computing devices and performs the method 500. Specifically, the method 500 will be described with respect to implementing step 410 of method 400.

In embodiments, the system receives 505 a set of similarity parameters and a pair of data vectors respectively representing attributes of a pair of patients. As previously described with reference to workflow 200, in some embodiments, each of the data vectors is generated by feature extraction based at least in part on the set of similarity parameters.

In embodiments, the system generates 510 a set of parameter-specific similarity factors using the pair of data vectors and a set of parameter-specific similarity functions respectively associated with the similarity parameters.

In some embodiments, each parameter-specific similarity factor is calculated/determined by applying a parameter-specific function to the pair of data vectors. For example, in some embodiments, a parameter-specific function may be a function that standardizes a metric representing its associated similarity parameter (e.g., Pearson correlation for numeric ratings, and/or Boolean preferences, e.g., Tanimoto similarity and log-likelihood) or a parameter-specific function may be a probabilistic function. Table 1 summarizes some exemplary similarity parameters and their associated parameter-specific functions.

TABLE 1

Exemplary parameter-specific functions

| Similarity Parameter | Metric | Standardization |
|---|---|---|
| Co-Morbidity | Log-likelihood of overlap of conditions | $1 - [1/(1 + \log L)]$ |
| Chronology | Correlation using array of onset ages of shared conditions | $[\rho + 1]/2$ |
| Rare Diseases | Joint probabilities of shared conditions, weighted by population prevalence | N/A |

In embodiments, the system calculates 515 a similarity metric representing the pair of data vectors as a linear sum of the set of parameter-specific similarity factors. In some embodiments, the similarity metric optionally may be normalized 520 to the range of 0,1.

Equation 1 is an exemplary calculation/determination of a similarity metric similarity$_{X,j}$ calculated/determined as a linear sum of parameter-specific similarity factors applied to a pair of healthcare feature vectors (the input patient vector X and a population patient vector j) and normalized to the range of 0,1:

$$\text{similarity}_{X,j} = f(\Sigma_{i=1}^{n} w_i * g_i[h_{X,j}]) \qquad \text{Equation 1}$$

where $f$ is the normalization function, i is the input similarity parameter, $h_{X,j}$ is the parameter-specific function associated with the input similarity parameter i, $g_i$ is the standardization of the parameter-specific function, if necessary, and $w_i$ is a weight associated with the input similarity parameter i. In some embodiments, each of the set of input similarity parameters may be associated with a weight that represents the relative importance of the similarity parameter to the requestor. In some embodiments, $w_i$ may be normalized to the range of 0,1.

Figure 6:
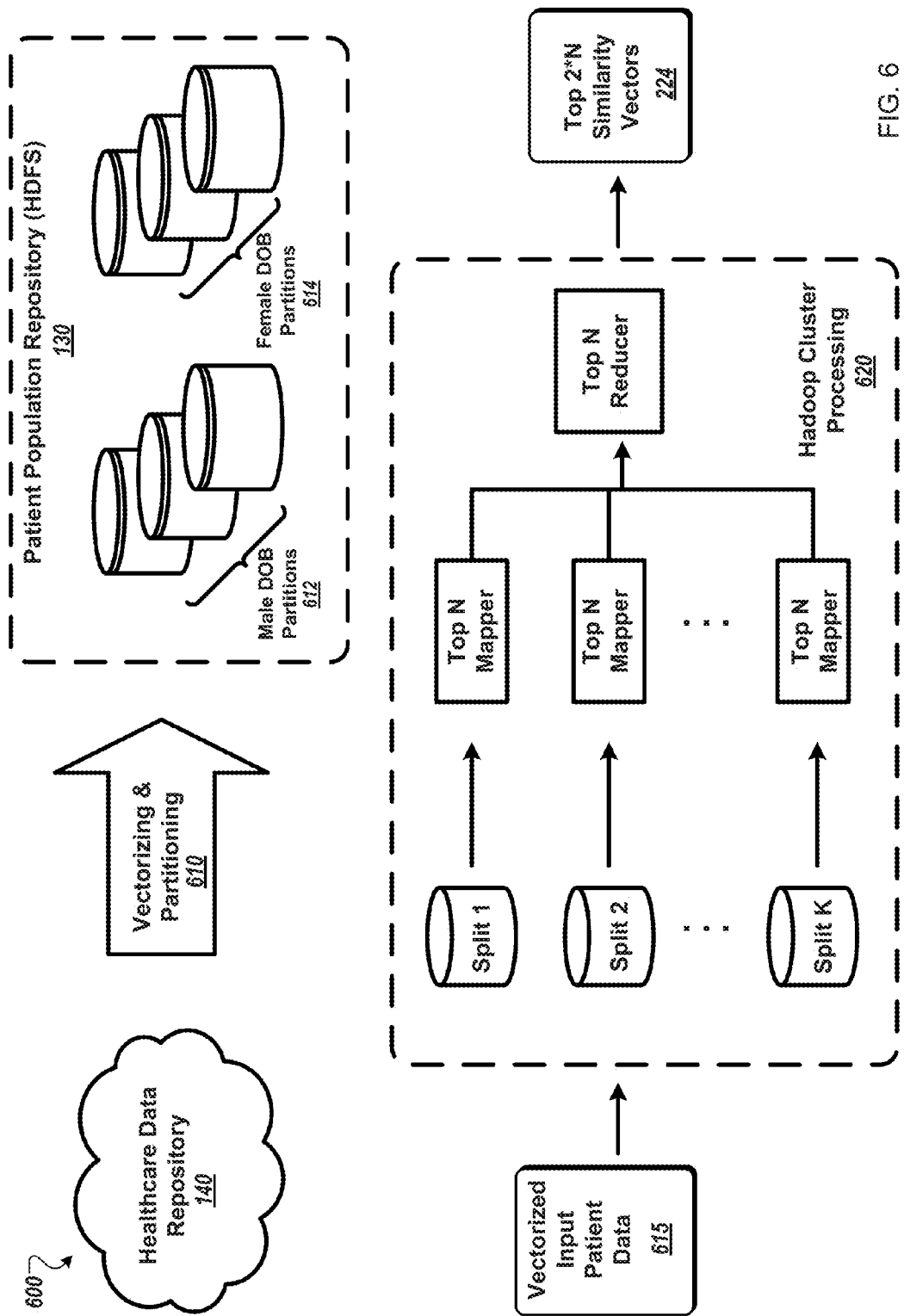
FIG. 6 illustrates a scenario for a parallel implementation of neighborhood generation associated with a particular patient in response to receiving a similarity request including attributes of the particular patient in accordance with some embodiments discussed herein.

FIG. 6 illustrates a scenario 600 for a parallel implementation of neighborhood generation associated with a particular patient in response to receiving a similarity request including attributes of the particular patient. In some embodiments, system 100 may be configured to execute scenario 600 while implementing method 400 and method 500. Scenario 600 is described for illustration and not limitation.

In embodiments, healthcare data that is collected from multiple data sources and stored in a healthcare data repository 140 is imported into a parallel distributed patient population repository 130, e.g., an instance of Hadoop Data File Services (HDFS). In embodiments, data importing includes vectorizing and partitioning 610 of the data. Thus, as illustrated, the data stored in the patient population repository may be partitioned according to age and gender of the patients. In some embodiments, the data stored in the patient population repository 130 may be updated regularly to reflect the current state of the data stored in the healthcare data repository 140.

In embodiments, neighborhood generation in response to a received similarity request may be performed as a parallel calculation. For example, in embodiments in which the patient population repository 130 is an instance of HDFS, the pairwise calculations of similarity metrics and then the selection of the neighborhood of population patients having attributes that are similar to an input patient may be implemented using Hadoop Cluster Processing 620.

As is well known in the art, Hadoop Cluster Processing is an implementation of MapReduce. The term MapReduce describes both a programming model and an implementation of the model for processing and generating large data sets. Using MapReduce, programmers specify a map function that processes input (key, value) pairs to generate a set of intermediate (key, value) pairs, and a reduce function that merges all intermediate values associated with the same intermediate key. Programs written in this functional style can automatically be parallelized and executed on a large cluster of commodity computers. The runtime system or framework can be implemented to partition the input data, schedule the program's execution across a set of machines, handle machine failures, and manage the required inter machine communication.

Typically, several map tasks operate independently on different processors (e.g., on different computing devices) and on different portions of input data. Similarly, several reduce tasks operate independently on a portion of the intermediate data. The portions of the intermediate data are partitioned according to the intermediate keys so that the same reducer operates on all values for a given intermediate key.

In the example implementation, the mapping tasks that a) compute similarity metrics by performing pairwise comparisons between the vectorized input patient data 615 and vectorized population patient data and b) rank the population patients based on their associated similarity values are split among the partitions in the patient population repository 130, and the reduce tasks that select the top-ranked population patients receive and consolidate the results of the mapping tasks.

Figure 7:
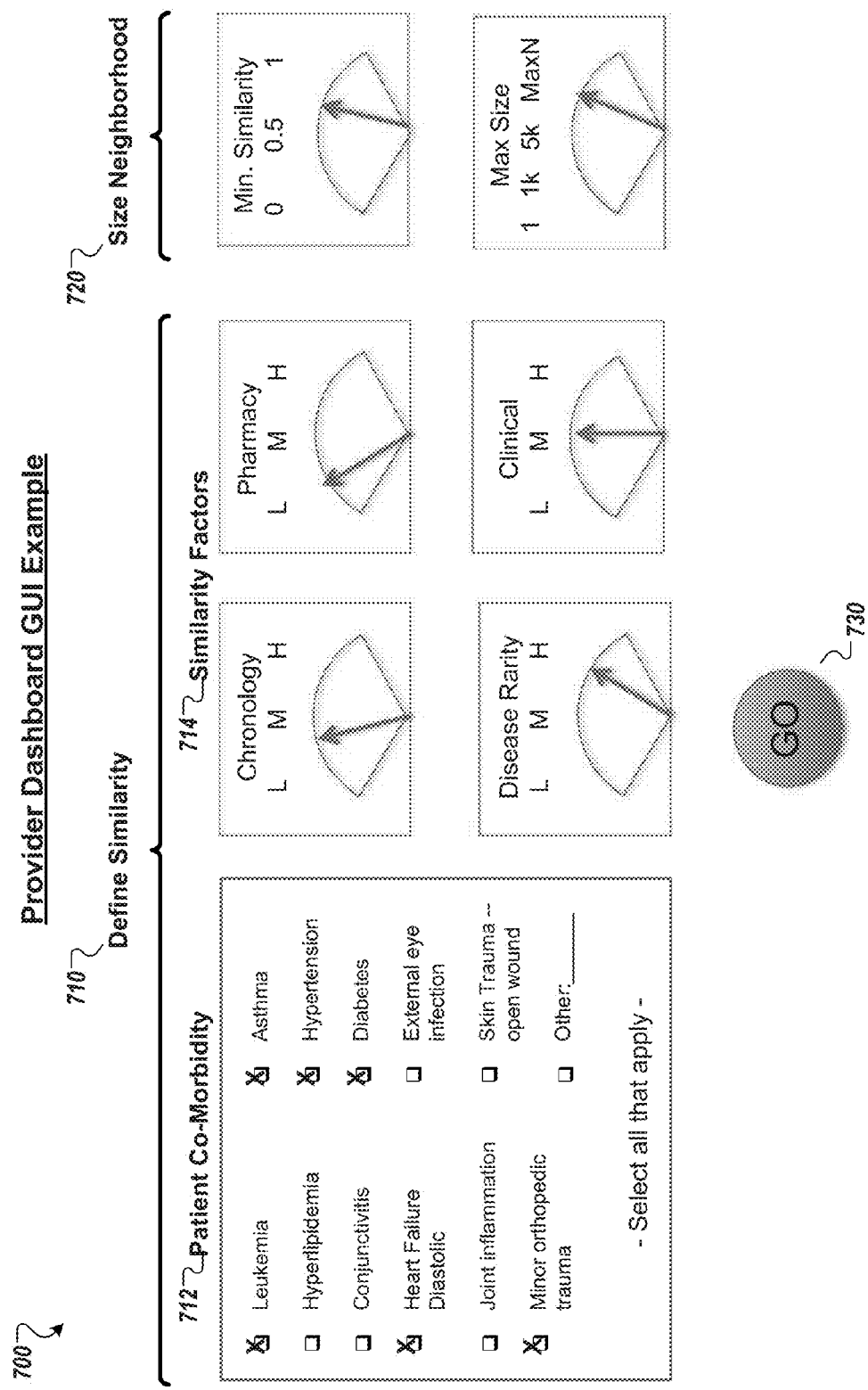
FIG. 7 illustrates an exemplary provider dashboard GUI that may be presented by a healthcare similarity client to a provider for similarity request data input in accordance with some embodiments discussed herein.

FIG. 7 illustrates an exemplary provider dashboard GUI 700 that may be presented by a healthcare similarity client to a provider for similarity request data input. In embodiments, provider dashboard GUI 700 may be implemented for data input as described with reference to workflow scenario 200. Provider dashboard GUI 700 is described for illustration and not limitation; the layout design (including the choice of widgets) and implementation are not critical to embodiments of the invention.

In embodiments, the layout of provider dashboard GUI 700 includes 3 interactive regions: similarity parameter input 710, neighborhood size parameter input 720, and similarity request submission input 730. In some embodiments, the information and choices displayed in the provider dashboard 700 may be customized to represent a particular application domain.

In the example, the similarity parameter input region 710 includes a region of patient co-morbidity 712 checkbox widgets through which a provider may select diseases applicable to a particular input patient. Thus, if provider dashboard GUI 700 were being used for input data in office visit workflow scenario 200, the displayed set of diseases may have been chosen to represent the most relevant healthcare considerations a physician might use for an application that generates a set of wellness recommendations for a particular patient.

In the example, the similarity parameter input region 710 also contains meter widgets 714 representing similarity factors other than patient co-morbidity. Instead of an either/or selection as would be made for each disease using a checkbox widget (e.g., the patient co-morbidity checkboxes 712), the user may use each widget to select, using the meter, a relative importance (e.g., Low, Medium, or High) for each of the similarity factors represented in this region. In some embodiments, the relative importance selection may be interpreted as a weight value to be associated with a similarity factor, as described previously with reference to method 500. In some alternative embodiments, the relative importance selection may be interpreted as a threshold for including the similarity factor in neighborhood generation (e.g., do not include a similarity factor in the set of input similarity factors if its relative importance is input as Low).

In the example, the neighborhood size parameter input region 720 includes meter widgets for user input of two different neighborhood size parameters: maximum neighborhood size and minimum similarity metric threshold to use in selecting patients to include in the neighborhood. A user may use the maximum size widget meter to specify a particular size desired for the generated neighborhood (e.g., 1, 1000, or 5000 patients) or "Max N" to specify the maximum number of patients identified as being similar to the input patient attributes. A user may use the minimum similarity widget meter to specify a minimum similarity metric threshold of 0 (i.e., no threshold), 0.5, or 1. In some embodiments, the system may provide default neighborhood size values to use in neighborhood generation, and at least some of the neighborhood size parameter selection widgets may enable a user to select values that override the default values.

In the example 700, the user may submit a similarity request to the system by selecting a "Go" button widget 730. In some embodiments, a provider dashboard GUI 700 may continue to display the input parameters selected by the user after the system has returned a result, enabling the user to modify at least some of the parameters and then generate a subsequent request. For example, a user may choose to increase maximum neighborhood size and/or decrease the minimum similarity threshold for a subsequent similarity request if the generated neighborhood size is insufficient for supporting the inferences being made by an application.

As described previous with reference to workflow 200, a study including one or more inferences 252 may be derived from attributes of the generated neighborhood, and the study may provide the basis for a variety of different types of healthcare applications.

FIG. 8 illustrates a "Focused Care for My Patient" application 800 in which the efficiency of the encounter between a provider/practitioner and a patient is improved (e.g., the provider is made aware of potential concerns/risk during a patient interview for identification of avoidable adverse/costly events).

Figure 10:
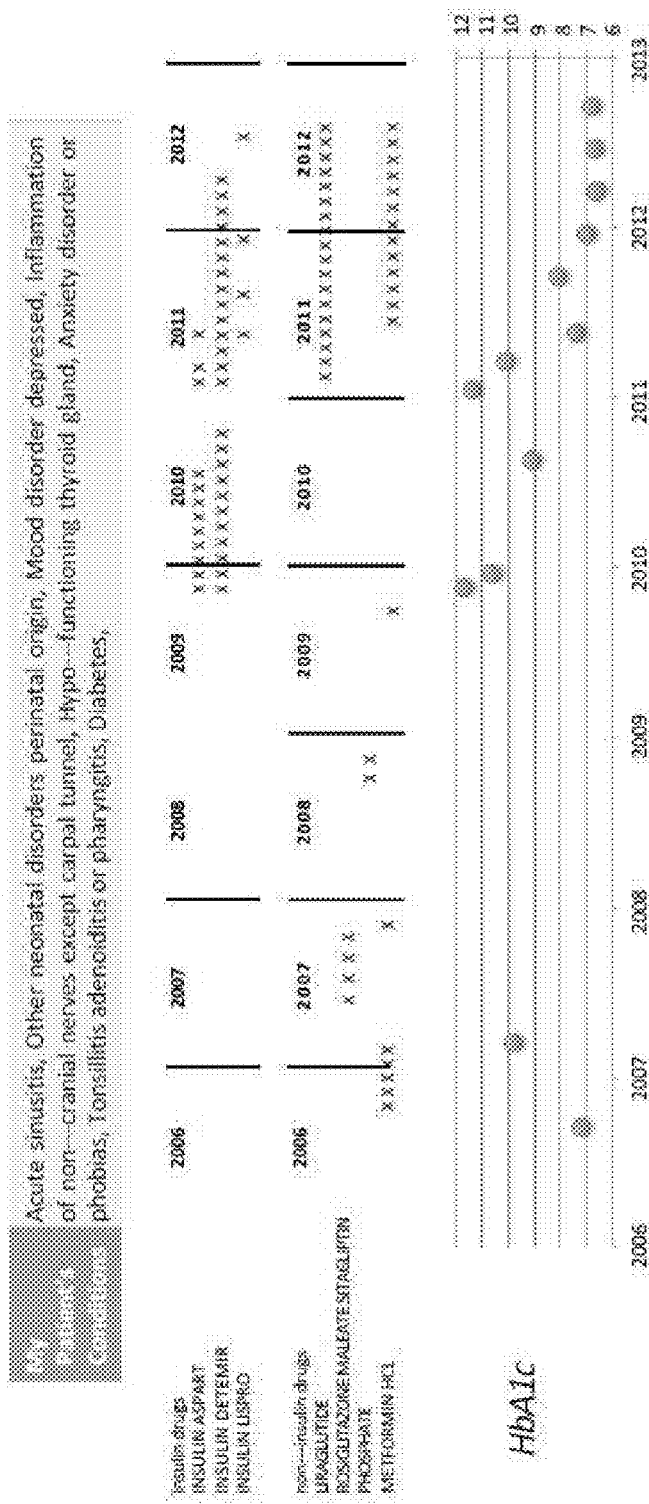
FIG. 10 illustrates an example of Treatment Optimization Clinical Pathways application in which a provider is informed as to how similar patient's treatments progressed and/or gaps in care may be highlighted in accordance with some embodiments discussed herein.

FIG. 9 and FIG. 10 respectively illustrate examples of Treatment Pathways 900 and Treatment Optimization Clinical Pathways 1000 applications in which a provider is informed as to how similar patient's treatments progressed and/or gaps in care may be highlighted (e.g., the provider/practitioner receives a summary of suggested procedures and/or treatments based on the commonality of similar patients and/or the probability of outcomes for each treatment found in the similar patients).

Figure 11:
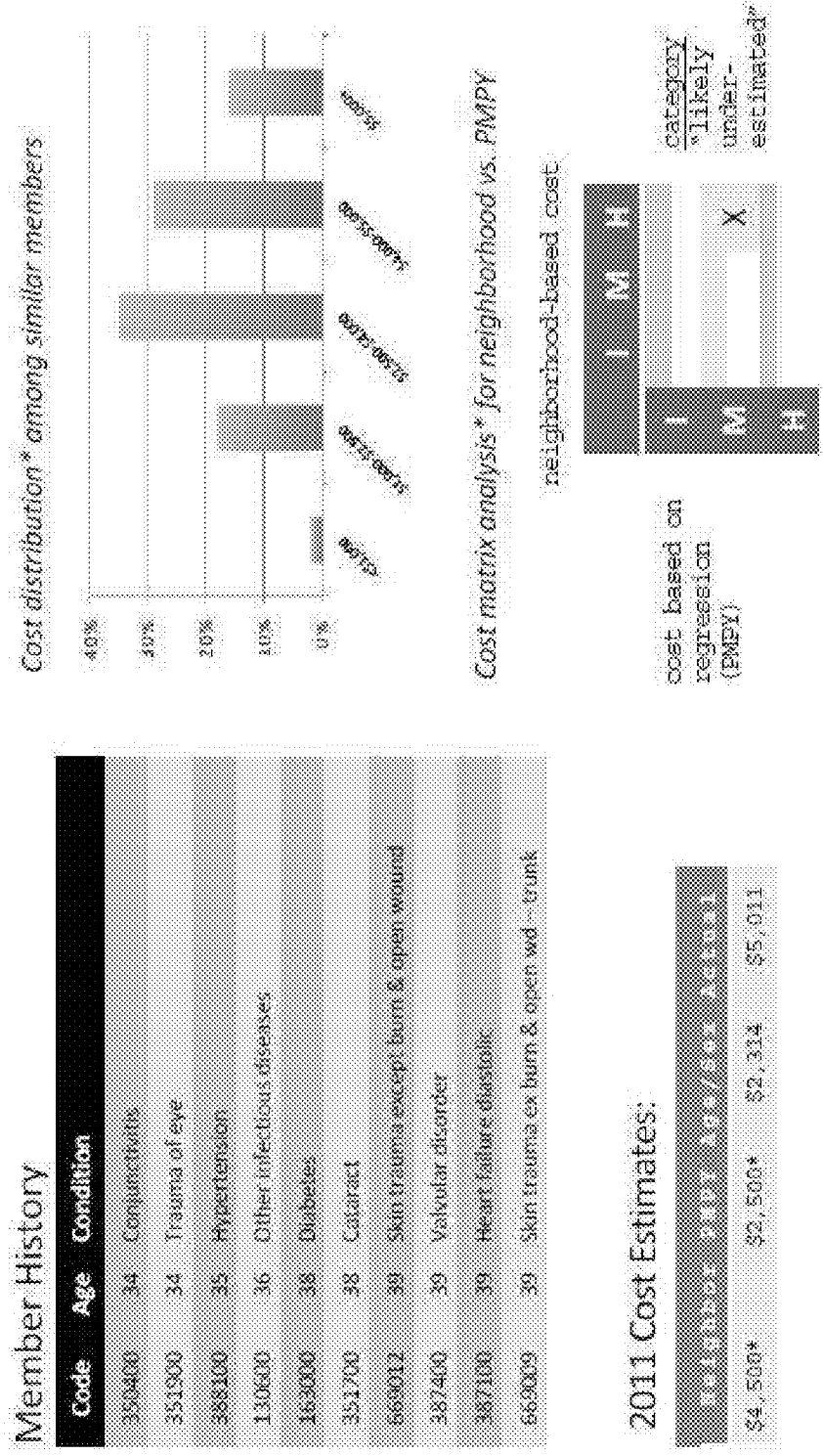
FIG. 11 illustrates an example Risk Adjustment application, in which the requestor is a healthcare plan.

FIG. 11 illustrates an example Risk Adjustment application 1100, in which the requestor is a healthcare plan (e.g., members are identified within a cohort who have elevated risk for an adverse/costly, yet avoidable event in the next 12 months that may not have been identified through population-based methods). Another healthcare plan application example (not illustrated) is Abuse (e.g., members or providers are identified who exhibit behaviors that are disjoint with their history and suggestive of abusive behavior, e.g., drug-seeking behaviors, doctor-shopping, and member ID fraud).

In other application examples, not illustrated, the requestor may be a patient 204 as described with reference to workflow 200 and/or a member of a healthcare plan, and the applications may include Health Improvement Scenarios (e.g., the patient 204 may compare him/herself to those with similar histories and receive suggestions on how changes in certain exposures, lifestyle, and/or habits may lead to an improved outlook, e.g., "if you attempt to get 8+ hours of sleep, you may lower the odds of getting lung cancer 12%," and "cutting down alcohol intake may lower your blood pressure 10 points"); and Provider Recommendations (e.g., a member who has been newly diagnosed with a given condition is presented with a list or providers with a history of treating similar patients ranked by geography and probability of outcomes for each treatment found in the similar patients).

Figure 12:
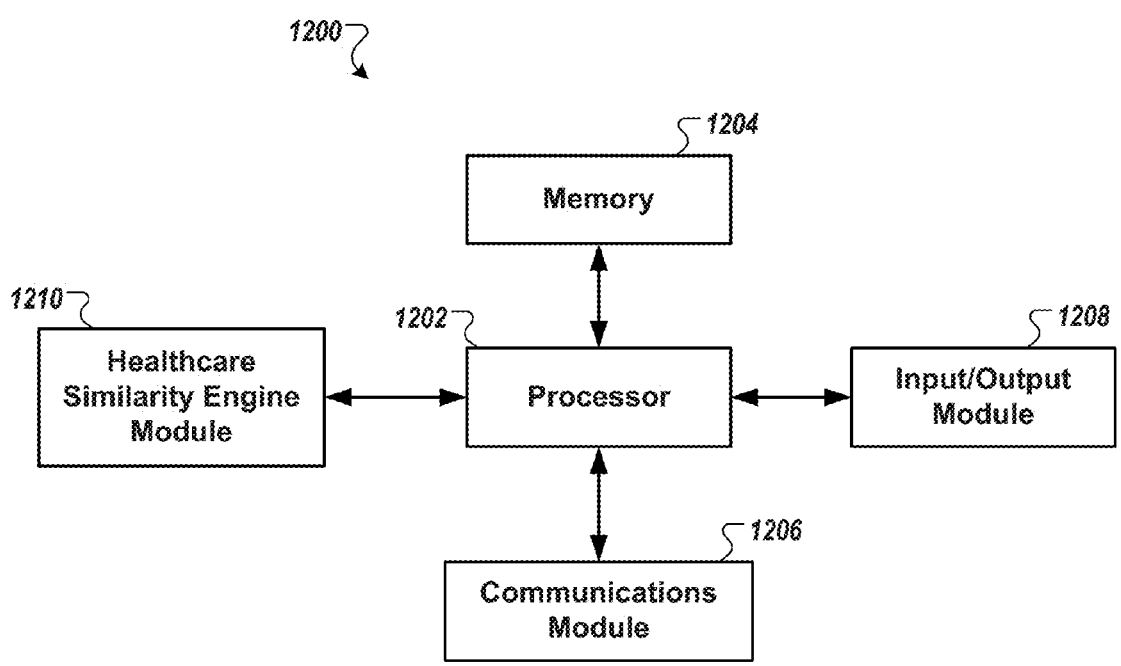
FIG. 12 illustrates a schematic block diagram of circuitry that can be included in a computing device, such as a healthcare similarity engine, in accordance with some embodiments discussed herein.

FIG. 12 shows a schematic block diagram of circuitry 1200, some or all of which may be included in, for example, healthcare similarity system 100. As illustrated in FIG. 12, in accordance with some example embodiments, circuitry 1200 can include various means, such as processor 1202, memory 1204, communications module 1206, and/or input/output module 1208. As referred to herein, "module" includes hardware, software and/or firmware configured to perform one or more particular functions. In this regard, the means of circuitry 1200 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 1204) that is executable by a suitably configured processing device (e.g., processor 1202), or some combination thereof.

Processor 1202 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 12 as a single processor, in some embodiments, processor 1202 comprises a plurality of processors. The plurality of processors may be embodied on a single computing device or may be distributed across a plurality of computing devices collectively configured to function as circuitry 1200. The plurality of processors may be in operative communication with each other and may be collectively configured to perform one or more functionalities of circuitry 1200 as described herein. In an example embodiment, processor 1202 is configured to execute instructions stored in memory 1204 or otherwise accessible to processor 1202. These instructions, when executed by processor 1202, may cause circuitry 1200 to perform one or more of the functionalities of circuitry 1200 as described herein.

Whether configured by hardware, firmware/software methods, or by a combination thereof, processor 1202 may comprise an entity capable of performing operations according to embodiments of the present invention while configured accordingly. Thus, for example, when processor 1202 is embodied as an ASIC, FPGA or the like, processor 1202 may comprise specifically configured hardware for conducting one or more operations described herein. Alternatively, as another example, when processor 1202 is embodied as an executor of instructions, such as may be stored in memory 1204, the instructions may specifically configure processor 1202 to perform one or more algorithms and operations described herein, such as those discussed in connection with FIGS. 4-5.

Memory 1204 may comprise, for example, volatile memory, non-volatile memory, or some combination thereof. Although illustrated in FIG. 12 as a single memory, memory 1204 may comprise a plurality of memory components. The plurality of memory components may be embodied on a single computing device or distributed across a plurality of computing devices. In various embodiments, memory 1204 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 1204 may be configured to store information, data (including analytics data), applications, instructions, or the like for enabling circuitry 1200 to carry out various functions in accordance with example embodiments of the present invention. For example, in at least some embodiments, memory 1204 is configured to buffer input data for processing by processor 1202. Additionally or alternatively, in at least some embodiments, memory 1204 is configured to store program instructions for execution by processor 1202. Memory 1204 may store information in the form of static and/or dynamic information. This stored information may be stored and/or used by circuitry 1200 during the course of performing its functionalities.

Communications module 1206 may be embodied as any device or means embodied in circuitry, hardware, a computer program product comprising computer readable program instructions stored on a computer readable medium (e.g., memory 1204) and executed by a processing device (e.g., processor 1202), or a combination thereof that is configured to receive and/or transmit data from/to another device, such as, for example, a second circuitry 1200 and/or the like. In some embodiments, communications module 1206 (like other components discussed herein) can be at least partially embodied as or otherwise controlled by processor 1202. In this regard, communications module 1206 may be in communication with processor 1202, such as via a bus. Communications module 1206 may include, for example, an antenna, a transmitter, a receiver, a transceiver, network interface card and/or supporting hardware and/or firmware/software for enabling communications with another computing device. Communications module 1206 may be configured to receive and/or transmit any data that may be stored by memory 1204 using any protocol that may be used for communications between computing devices. Communications module 1206 may additionally or alternatively be in communication with the memory 1204, input/output module 1208 and/or any other component of circuitry 1200, such as via a bus.

Input/output module 1208 may be in communication with processor 1202 to receive an indication of a user input and/or to provide an audible, visual, mechanical, or other output to a user. Some example visual outputs that may be provided to a user by circuitry 1200 are discussed in connection with FIG. 1 and FIG. 7. As such, input/output module 1208 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 1200 is embodied as a server or database, aspects of input/output module 1208 may be reduced as compared to embodiments where circuitry 1200 is implemented as an end-user machine or other type of device designed for complex user interactions. In some embodiments (like other components discussed herein), input/output module 1208 may even be eliminated from circuitry 1200. Alternatively, such as in embodiments wherein circuitry 1200 is embodied as a server or database, at least some aspects of input/output module 1208 may be embodied on an apparatus used by a user that is in communication with circuitry 1200. Input/output module 1208 may be in communication with the memory 1204, communications module 1206, and/or any other component(s), such as via a bus. Although more than one input/output module and/or other component can be included in circuitry 1200, only one is shown in FIG. 12 to avoid overcomplicating the drawing (like the other components discussed herein).

Healthcare similarity engine module 1210 may also or instead be included and configured to perform the functionality discussed herein related to the healthcare similarity engine 102 discussed above. In some embodiments, some or all of the functionality of healthcare similarity engine may be performed by processor 1202. In this regard, the example processes and algorithms discussed herein can be performed by at least one processor 1202 and/or healthcare similarity engine module 1210. For example, non-transitory computer readable media can be configured to store firmware, one or more application programs, and/or other software, which include instructions and other computer-readable program code portions that can be executed to control each processor (e.g., processor 1202 and/or healthcare similarity engine module 1210) of the components of system 100 to implement various operations, including the examples shown above. As such, a series of computer-readable program code portions are embodied in one or more computer program products and can be used, with a computing device, server, and/or other programmable apparatus, to produce machine-implemented processes.

Any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of system 100. In some embodiments, one or more external systems (such as a remote cloud computing and/or data storage system) may also be leveraged to provide at least some of the functionality discussed herein.

As described above in this disclosure, aspects of embodiments of the present invention may be configured as methods, mobile devices, backend network devices, and the like.

Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments of the present invention have been described above with reference to block diagrams and flowchart illustrations of methods, apparatuses, systems and computer program products. It will be understood that each block of the circuit diagrams and process flow diagrams, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 1202 and/or healthcare similarity engine module 1210 discussed above with reference to FIG. 12, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 1204) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method for generating a similarity request and causing display of a similarity presentation via an interactive user interface, comprising:

causing display of, by a computing entity, an interactive user interface comprising a graphical representation of a healthcare similarity request input dashboard, wherein the graphical representation comprises a similarity parameter input region, a neighborhood size parameter input region, and a similarity request input region; and responsive to user-interaction with the similarity request input region, transmitting, by the computing entity, a similarity request for a healthcare similarity system, the similarity request comprising (a) patient X data representing attributes of a particular patient X, (b) a set of one or more similarity parameters input or selected via the similarity parameter input region, and (c) at least one neighborhood size parameter input or selected via the neighborhood size parameter input region, the neighborhood size parameter (i) defining a maximum distance in a multidimensional space and (ii) controlling a neighborhood subset of a population of patients provided in a similarly presentation; and receiving a similarity presentation provided by the healthcare similarity system, wherein the healthcare similarity system:

generates a set of pairwise similarity metrics for patient X and each patient of a plurality of patients within the population of patients by determining, based at least in part on the set of one or more similarity parameters and one or more parameter-specific functions, a respective distance between (a) a patient X data vector in the multidimensional space determined from the patient X data and (b) a respective data vector in the multidimensional space for each patient within the population of patients, wherein each pairwise similarity metric respectively represents the similarity between patient X and the corresponding patient within the population of patients, ranks the patients within the population of patients based on their respective similarity metrics, generates the similarity presentation comprising the neighborhood subset of the population of patients most similar to patient X, wherein (a) the neighborhood subset size is based at least in part on the neighborhood size parameter defining the maximum distance in the multidimensional space between the patient X data vector and the respective data vector for each patient within the population of patients, and (b) the similarity presentation is for deriving at least one inference based at least in part on attributes of the subset of the population of patients most similar to patient X, and transmits the similarity presentation for the computing entity; and causing display of, by the computing entity, the interactive user interface comprising the similarity presentation provided by the healthcare similarity system.

2. The method of claim 1, wherein the similarity parameter input region comprises similarity widgets representing one or more similarity parameters.

3. The method of claim 2, wherein the similarity widgets comprise a patient co-morbidity region comprising a set of checkbox widgets each associated with a particular disease.

4. The method of claim 2, wherein the similarity widgets comprise at least one meter widget associated with a particular similarity parameter, and wherein the meter represents a relative importance of the particular similarity parameter.

5. The method of claim 4, wherein adding the particular similarity parameter to the set of one or more similarity parameters comprises a weight associated with a particular similarity parameter based on a user-selected importance indicator represented by the at least one meter.

6. The method of claim 1, wherein the neighborhood size parameter input region comprises at least one neighborhood size widget representing at least one neighborhood size parameter.

7. The method of claim 6, wherein the neighborhood size widget is a meter widget and the neighborhood size parameter is maximum neighborhood size.

8. The method of claim 6, wherein the neighborhood size widget is a meter widget and the neighborhood size parameter is minimum similarity metric threshold.

9. An apparatus comprising at least one processor and at least one memory including program code, the at least one memory and the program code configured to, with the processor, cause the apparatus to at least:

cause display of an interactive user interface comprising a graphical representation of a healthcare similarity request input dashboard, wherein the graphical representation comprises a similarity parameter input region, a neighborhood size parameter input region, and a similarity request input region; and responsive to user-interaction with the similarity request input region, transmit a similarity request for a healthcare similarity system, the similarity request comprising (a) patient X data representing attributes of a particular patient X, (b) a set of one or more similarity parameters input or selected via the similarity parameter input region, and (c) at least one neighborhood size parameter input or selected via the neighborhood size parameter input region, the neighborhood size parameter (i) defining a maximum distance in a multidimensional space and (ii) controlling a neighborhood subset of a population of patients provided in a similarly presentation; and receive a similarity presentation provided by the healthcare similarity system, wherein the healthcare similarity system:

generates a set of pairwise similarity metrics for patient X and each patient of a plurality of patients within the population of patients by determining, based at least in part on the set of one or more similarity parameters and one or more parameter-specific functions, a respective distance between (a) a patient X data vector in the multidimensional space determined from the patient X data and (b) a respective data vector in the multidimensional space for each patient within the population of patients, wherein each pairwise similarity metric respectively represents the similarity between patient X and the corresponding patient within the population of patients, ranks the patients within the population of patients based on their respective similarity metrics, generates the similarity presentation comprising the neighborhood subset of the population of patients most similar to patient X, wherein (a) the neighborhood subset size is based at least in part on the neighborhood size parameter defining the maximum distance in the multidimensional space between the patient X data vector and the respective data vector for each patient within the population of patients, and (b) the similarity presentation is for deriving at least one inference based at least in part on attributes of the subset of the population of patients most similar to patient X, and transmits the similarity presentation for the computing entity; and cause display of the interactive user interface comprising the similarity presentation provided by the healthcare similarity system.

10. The apparatus of claim 9, wherein the similarity parameter input region comprises similarity widgets representing one or more similarity parameters.

11. The apparatus of claim 10, wherein the similarity widgets comprise a patient co-morbidity region comprising a set of checkbox widgets each associated with a particular disease.

12. The apparatus of claim 10, wherein the similarity widgets comprise at least one meter widget associated with a particular similarity parameter, and wherein the meter represents a relative importance of the particular similarity parameter.

13. The apparatus of claim 12, wherein adding the particular similarity parameter to the set of one or more similarity parameters comprises a weight associated with a particular similarity parameter based on a user-selected importance indicator represented by the at least one meter.

14. The apparatus of claim 9, wherein the neighborhood size parameter input region comprises at least one neighborhood size widget representing at least one neighborhood size parameter.

15. A computer program product for generating a similarity request and causing display of a similarity presentation via an interactive user interface, the computer program product stored on a non-transitory computer readable medium, comprising instructions that when executed on one or more computers cause the one or more computers to perform operations comprising:

causing display of an interactive user interface comprising a graphical representation of a healthcare similarity request input dashboard, wherein the graphical representation comprises a similarity parameter input region, a neighborhood size parameter input region, and a similarity request input region; and responsive to user-interaction with the similarity request input region, transmitting a similarity request for a healthcare similarity system, the similarity request comprising (a) patient X data representing attributes of a particular patient X, (b) a set of one or more similarity parameters input or selected via the similarity parameter input region, and (c) at least one neighborhood size parameter input or selected via the neighborhood size parameter input region, the neighborhood size parameter (i) defining a maximum distance in a multidimensional space and (ii) controlling a neighborhood subset of a population of patients provided in a similarly presentation; and receiving a similarity presentation provided by the healthcare similarity system, wherein the healthcare similarity system:

generates a set of pairwise similarity metrics for patient X and each patient of a plurality of patients within the population of patients by determining, based at least in part on the set of one or more similarity parameters and one or more parameter-specific functions, a respective distance between (a) a patient X data vector in the multidimensional space determined from the patient X data and (b) a respective data vector in the multidimensional space for each patient within the population of patients, wherein each pairwise similarity metric respectively represents the similarity between patient X and the corresponding patient within the population of patients, ranks the patients within the population of patients based on their respective similarity metrics, generates the similarity presentation comprising the neighborhood subset of the population of patients most similar to patient X, wherein (a) the neighborhood subset size is based at least in part on the neighborhood size parameter defining the maximum distance in the multidimensional space between the patient X data vector and the respective data vector for each patient within the population of patients, and (b) the similarity presentation is for deriving at least one inference based at least in part on attributes of the subset of the population of patients most similar to patient X, and transmits the similarity presentation for the computing entity; and causing display of the interactive user interface comprising the similarity presentation provided by the healthcare similarity system.

16. The computer program product of claim 15, wherein the similarity parameter input region comprises similarity widgets representing one or more similarity parameters.

17. The computer program product of claim 16, wherein the similarity widgets comprise a patient co-morbidity region comprising a set of checkbox widgets each associated with a particular disease.

18. The computer program product of claim 16, wherein the similarity widgets comprise at least one meter widget associated with a particular similarity parameter, and wherein the meter represents a relative importance of the particular similarity parameter.

19. The computer program product of claim 18, wherein adding the particular similarity parameter to the set of one or more similarity parameters comprises a weight associated with a particular similarity parameter based on a user-selected importance indicator represented by the at least one meter.

20. The computer program product of claim 15, wherein the neighborhood size parameter input region comprises at least one neighborhood size widget representing at least one neighborhood size parameter.

* * * * *